United States Patent
Barias et al.

(10) Patent No.: US 11,939,289 B2
(45) Date of Patent: Mar. 26, 2024

(54) PROCESS FOR THE CONTROLLED OLIGOMERIZATION OF BUTENES

(71) Applicant: LUMMUS TECHNOLOGY LLC, Houston, TX (US)

(72) Inventors: Rosette Barias, Houston, TX (US); Liang Chen, Houston, TX (US); Michael Jon Scott, Houston, TX (US)

(73) Assignee: LUMMUS TECHNOLOGY LLC, Houston, TX (US)

( * ) Notice: Subject to any disclaimer, the term of this patent is extended or adjusted under 35 U.S.C. 154(b) by 0 days.

(21) Appl. No.: 18/148,103

(22) Filed: Dec. 29, 2022

(65) Prior Publication Data

US 2023/0133823 A1 May 4, 2023

Related U.S. Application Data

(63) Continuation-in-part of application No. PCT/US2021/039595, filed on Jun. 29, 2021.

(Continued)

(51) Int. Cl.
*C07C 7/177* (2006.01)
*B01D 3/00* (2006.01)
(Continued)

(52) U.S. Cl.
CPC .............. *C07C 7/177* (2013.01); *B01D 3/009* (2013.01); *B01D 3/141* (2013.01); *B01D 3/143* (2013.01);
(Continued)

(58) Field of Classification Search
CPC .. C07C 7/04; C07C 7/177; C07C 2/08; C07C 2/16; C07C 2/28; C07C 5/03;
(Continued)

(56) References Cited

U.S. PATENT DOCUMENTS

| 3,960,978 A | 6/1976 | Givens et al. |
| 4,021,502 A | 5/1977 | Plank et al. |

(Continued)

FOREIGN PATENT DOCUMENTS

| EP | 1940756 B1 | 8/2012 |
| WO | 0151435 A1 | 7/2001 |
| WO | 2020092774 A1 | 5/2020 |

OTHER PUBLICATIONS

Doherty et al. ("Distillation." Chap. 13.0 in Perry's Chemical Engineers' Handbook. 7th ed., 2008). (Year: 2008).*

(Continued)

*Primary Examiner* — In Suk C Bullock
*Assistant Examiner* — Jason Y Chong
(74) *Attorney, Agent, or Firm* — Osha Bergman Watanabe & Burton LLP

(57) ABSTRACT

The selective dimerization of isoolefins, such as isobutene or isopentane, or mixtures thereof, may be conducted in a system including a series of fixed bed reactors and a catalytic distillation reactor. The system may provide for conveyance of the fixed bed reactor effluents, without componential separation, to a downstream reactor. It has been found that a high selectivity to the dimer may be achieved even though intermediate separation of the desired product from unreacted components between reactors is not performed. Further, embodiments provide for use of a divided wall column for recovery of a high purity dimer product, reducing unit piece count and plot size.

9 Claims, 5 Drawing Sheets

Related U.S. Application Data

(60) Provisional application No. 63/045,658, filed on Jun. 29, 2020.

(51) Int. Cl.
*B01D 3/14* (2006.01)
*B01J 8/04* (2006.01)
*C07C 2/08* (2006.01)
*C07C 2/16* (2006.01)
*C07C 5/03* (2006.01)

(52) U.S. Cl.
CPC .............. *B01J 8/0419* (2013.01); *C07C 2/08* (2013.01); *C07C 2/16* (2013.01); *C07C 5/03* (2013.01); *C07C 2527/03* (2013.01)

(58) Field of Classification Search
CPC ..... C07C 2527/03; C07C 11/02; B01D 3/009; B01D 3/141; B01D 3/143; B01J 8/0419; B01J 8/0457; Y02P 20/10
See application file for complete search history.

(56) References Cited

U.S. PATENT DOCUMENTS

| | | | |
|---|---|---|---|
| 4,100,220 A | 7/1978 | Bowman et al. | |
| 4,242,530 A | 12/1980 | Smith, Jr. | |
| 4,331,824 A | 5/1982 | Ikeda et al. | |
| 4,375,576 A | 3/1983 | Smith, Jr. | |
| 4,551,567 A | 11/1985 | Smith, Jr. | |
| 4,629,710 A | 12/1986 | Smith, Jr. | |
| 5,003,124 A | 3/1991 | Smith, Jr. et al. | |
| 5,877,372 A | 3/1999 | Evans et al. | |
| 6,335,473 B1 | 1/2002 | Bakshi et al. | |
| 6,376,731 B1 | 4/2002 | Evans et al. | |
| 6,689,927 B1 | 2/2004 | Frame et al. | |
| 6,774,275 B2 | 8/2004 | Smith, Jr. et al. | |
| 6,858,770 B2 | 2/2005 | Smith, Jr. et al. | |
| 6,936,742 B2 | 8/2005 | Smith, Jr. | |
| 6,995,296 B2 | 2/2006 | Smith, Jr. et al. | |
| 7,145,049 B2 | 12/2006 | Loescher et al. | |
| 7,250,542 B2 | 7/2007 | Smith, Jr. et al. | |
| 7,288,693 B2 | 10/2007 | Smith, Jr. et al. | |
| 7,319,180 B2 | 1/2008 | Smith, Jr. et al. | |
| 8,134,039 B2 * | 3/2012 | Di Girolamo | C07C 9/21 |
| | | | 44/449 |
| 8,188,327 B1 | 5/2012 | Bakshi | |
| 2004/0006252 A1 | 1/2004 | Smith | |
| 2004/0210093 A1 | 10/2004 | Groten et al. | |
| 2006/0030741 A1 | 2/2006 | Smith et al. | |
| 2007/0161843 A1 | 7/2007 | Smith et al. | |
| 2008/0045763 A1 | 2/2008 | Cross et al. | |
| 2008/0064911 A1 | 3/2008 | Loescher et al. | |
| 2010/0137668 A1 | 6/2010 | Loescher et al. | |

OTHER PUBLICATIONS

International Search Report issued in corresponding International Application No. PCT/US2021/039595 dated Oct. 22, 2021 (3 pages).
Written Opinion issued in corresponding International Application No. PCT/US2021/039595 dated Oct. 22, 2021 (5 pages).

* cited by examiner

PROCESS FOR THE CONTROLLED OLIGOMERIZATION OF BUTENES

BACKGROUND

In order to meet the fuel blending requirements, such as octane rating or vapor pressure requirements, smaller olefin molecules may be upgraded to produce longer chain molecules. Alternatively, the smaller olefin molecules may be etherified so as to increase the oxygen content of the molecule and the resulting fuel blend.

One commonly used method of upgrading smaller olefin molecules, such as $C_2$ to $C_5$ olefins, is an oligomerization reaction. Isobutene is commercially significant in many applications. For example, isobutene is one of the comonomers in butyl rubber. Isobutene can also be oligomerized to produce compounds that can be used as chemical feedstock for further reacting or in gasoline blending. Diisobutene, the isobutene dimer, is of particular commercial value in several applications. For example, diisobutene can be used as an alkylation reaction feedstock or as an intermediate in the preparation of detergents. Diisobutene can also be hydrogenated to pure isooctane (2,2,4-tri-methyl pentane) that is highly preferred in gasoline blending.

Oligomerization reactions involve contacting an olefin with a catalyst in order to produce a longer chain molecule. An oligomer can consist of two or more constituent olefin molecules. For example, dimerization is a type of oligomerization reaction that is limited to a combination of only two olefin molecules. If the olefin feed contains only one type of olefin, a dimer product is formed. If the olefin feed contains two or more different olefins or olefin isomers, a codimer product may also be formed.

Specifically, $C_4$ olefin dimerization is widely used for producing isooctene, an intermediate that can be hydrogenated to produce isooctane, a high-value gasoline blending additive. Several representative olefin dimerization reactions are shown below:

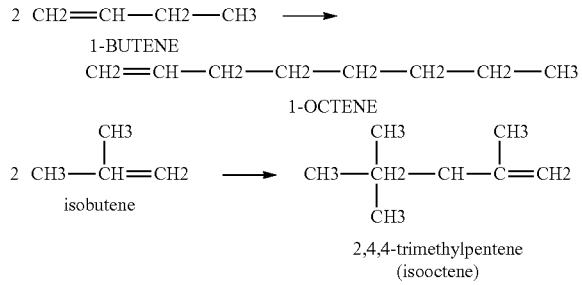

A gas phase olefin oligomerization process is disclosed in U.S. Pat. Nos. 3,960,978 and 4,021,502, where $C_2$ to $C_5$ olefins, fed as either pure olefins or in admixture with paraffins, are oligomerized via contact with a zeolite fixed catalyst bed. Other oligomerization processes are disclosed in, for example, U.S. Pat. Nos. 4,242,530, 4,375,576, 5,003,124, 7,145,049, 6,335,473, 6,774,275, 6,858,770, 6,936,742, 6,995,296, 7,250,542, 7,288,693, 7,319,180, 6,689,927, 6,376,731, 5,877,372, 4,331,824, 4,100,220 and U.S. Patent Application Publication Nos. 20080064911, 20080045763, 20070161843, 20060030741, 20040210093, and 20040006252, among others. Acid resin catalysts have also found use in various other petrochemical processes, including formation of ethers, hydration of olefins, esterifications, and epoxidations, such as those described in U.S. Pat. Nos. 4,551,567 and 4,629,710.

Processes for oligomerization of olefins over such resin catalysts require periodic shutdowns of the oligomerization unit to replace and/or regenerate the catalysts. Further, such solid-catalyzed processes may require additives ("selectivators" or "moderators" as used interchangeably herein) to promote the selectivity of the catalyst to the dimer, where the additives may result in unwanted acid throw, deactivating the catalyst, as well as byproducts, and may additionally require complicated separation processes to remove the additive and/or the byproducts from the resulting product streams.

In any type of oligomerization reaction, the oligomerization catalyst activity can be drastically reduced due to poisoning, fouling, and coking frequently caused by impurities present in the olefin feed stream. Furthermore, various additives and impurities that may be present in the olefin feed can participate inside reactions, leading to formation of undesirable byproducts. For example, the presence of normal butene in the isobutene oligomerization process to produce isooctene dimer can lead to formation of undesirable $C_8$ codimers. Formation of $C_8$ codimers can adversely affect an operator in two major ways. First, it reduces the effective yield of the $C_8$ dimer target product, thus increasing the dimerization reactor feedstock and operating costs. Second, it may require additional costs associated with separation and removal of $C_8$ codimers from the $C_8$ dimer product.

Oligomerization reaction additives, such as a reaction moderator, can also participate in undesirable side reactions with the olefin or with the dimerization product. Moderator is frequently added to the oligomerization reaction in order to increase the dimer selectivity by limiting the extent of oligomerization reaction to the dimer stage. Suitable moderators include oxygenates, such as water, primary, secondary and tertiary alcohols and ethers. However, as a trade-off to achieving high dimer selectivity, a portion of the moderator can react with an olefin or a dimerization product to form heavy oxygenates, for example, MSBE. A representative reaction of an olefin with a moderator to form a heavy oxygenate is shown below:

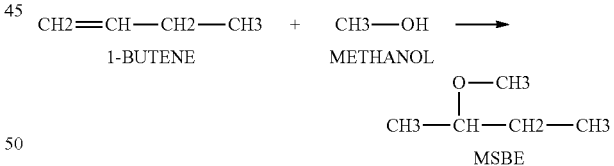

Similar to other types of side reactions, the reaction of moderator to produce heavy oxygenates, such as MSBE, can also reduce the $C_8$ dimer product yield and require additional separation costs in order to maintain the desired product purity.

SUMMARY OF THE CLAIMED EMBODIMENTS

In one aspect, embodiments herein relate to processes for the dimerization of olefins and/or isoolefins. The processes may include feeding an oxygenate reaction modifier and a hydrocarbon feed to a fixed bed reactor containing an oligomerization catalyst. In some embodiments, the hydrocarbon feed may include isobutene. In the fixed bed reactor, the process may include reacting isobutene at oligomerization conditions to form a reaction effluent comprising reaction modifier, isobutene dimers, and unreacted isobutene. Following effluent recovery, and without componential separation, the process includes feeding the reaction effluent to a second fixed bed reactor containing an oligomerization catalyst and reacting isobutene in the second fixed bed reactor at oligomerization conditions to form additional isobutene dimers, recovering a second reaction effluent comprising reaction modifier, isobutene dimers, any oxygenate high-boiling reaction byproducts formed, as well as any unreacted isobutane. Following recovery of the second reaction effluent, and without intermediate componential separation, the process includes feeding the second reaction effluent to a catalytic distillation reactor having a reactive distillation zone comprising an oligomerization catalyst. Concurrently within the catalytic distillation reactor, the process includes: reacting unreacted isobutene in the second reaction effluent to form additional isobutene dimers; separating the dimers and any oxygenate high-boiling reaction byproducts, recovered as a bottoms fraction, from the isobutane and any unreacted isobutene recovered as an overheads fraction.

In embodiments where the bottoms fraction further comprises reaction modifier and isoolefin trimers, the system may further include a divided wall distillation column for separating the bottoms fraction and to recover an overheads fraction, a side draw fraction comprising the isoolefin dimers, and a bottoms fraction comprising the isoolefin trimers.

DETAILED DESCRIPTION

Figure 1:
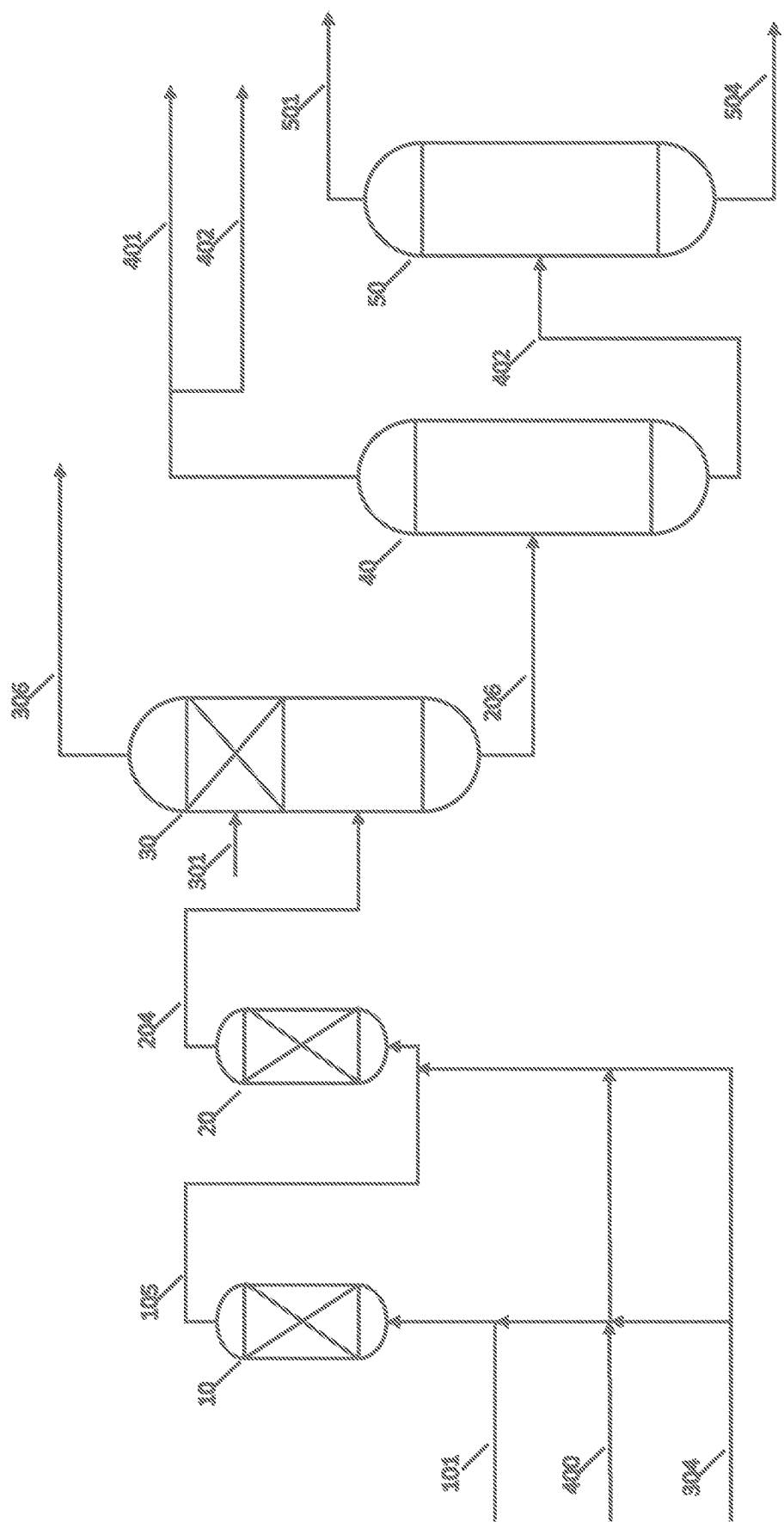
FIG. 1 is a simplified process flow diagram of a system for dimerization and/or oligomerization of olefins according to embodiments herein.

Embodiments herein relate generally to dimerization and/or oligomerization of olefins. In certain embodiments of the present disclosure, $C_4$ olefins, such as 1-butene, 2-butene, and/or isobutene, undergo a controlled dimerization or oligomerization process in a series reactor configuration, a portion of which includes a catalytic distillation reactor system, where the reaction is carried out in the presence of oxygenates, such as alcohols, under mild conditions.

As used in embodiments disclosed herein, "catalytic distillation reactor system" and like terms refers to a system for concurrently or simultaneously reacting compounds and separating the reactants and the products using fractional distillation. In some embodiments, the catalytic distillation reactor system may comprise a conventional catalytic distillation column reactor, where the reaction and distillation are concurrently taking place at boiling point conditions. In other embodiments, the catalytic distillation reactor system may comprise a distillation column combined with at least one side reactor, where the side reactor may be operated as a liquid phase reactor or a boiling point reactor. Both catalytic distillation reactor systems described may be preferred over conventional liquid phase reaction followed by separations, a catalytic distillation column reactor may have the advantages of decreased piece count, reduced capital cost, increased catalyst productivity per pound of catalyst, efficient heat removal (heat of reaction may be absorbed into the heat of vaporization of the mixture), and a potential for shifting equilibrium. Divided wall distillation columns, where at least one section of the divided wall column contains a catalytic distillation structure, may also be used, and are considered "catalytic distillation reactor systems" herein.

The hydrocarbon feed to the reactor(s) may include purified isoolefin streams, such as a feed stream containing, isobutene, isoamylenes, or mixtures thereof. In other embodiments, the hydrocarbon feed to the reactor(s) may include purified n-olefin streams, such as a feed stream containing 1-butene, 2-butene, 1-pentene, 2-pentene, or mixtures thereof. In other embodiments, hydrocarbon feeds may include a $C_4$-$C_5$, a $C_4$ or a $C_5$ light naphtha cut. When present in mixtures, the tertiary olefins, such as isobutene and isoamylenes, are more reactive than the normal olefin isomers and are preferentially reacted (dimerized, oligomerized, or etherified). The alkanes and isoalkanes in the $C_4$ to $C_5$ light naphtha cuts may include n-butane, n-pentane, isobutane, isopentane or mixtures thereof, which may act as a diluent in the reactors. In some embodiments, such diluents may be added to the reaction system separately from the purified isoolefin stream.

In some embodiments, a C4-containing hydrocarbon stream, such as a C4 naphtha cut, a C4-C5 naphtha cut, or a C4-C6 naphtha cut may be fed to a reactor for the hydroisomerization of 1-butene to 2-butene, thus allowing for the separation of isobutene from the linear olefin 2-butene, providing a mixture rich in isobutene, if desired. The hydroisomerization may be carried out in a fixed bed reactor as well as in a catalytic distillation reaction system. For example, in some embodiments, a feed containing 1-butene, 2-butene, isobutene, n-butane, and isobutane may be fed to a catalytic distillation reaction system containing at least one bed of hydroisomerization catalyst for the concurrent hydroisomerization of 1-butene to 2-butene and the fractionation of isobutane and isobutene, recovered as an overheads fraction, from the heavier hydrocarbons in the feed stream, including the n-butane and 2-butene, recovered as a bottoms fraction. Feed and catalyst locations may be positioned so as to preferentially contact the 1-butene with the hydroisomerization catalyst. For example, the hydrocarbon may be fed to a location below the hydroisomerization catalyst, allowing the 1-butene to distill up into the catalyst bed while distilling the 2-butene down the column, away from the catalyst bed. In other embodiments, a hydroisomerized effluent from a fixed bed reactor may be fed to a conventional distillation column to result in similar overheads and bottoms fractions.

The resulting bottoms fraction, including the 2-butene and the n-butane, may be lean in 1-butene, isobutane, and isobutene. For example, depending upon the severity of the distillation conditions used, the bottoms fraction may contain less than 1 weight percent total of 1-butene, isobutane, and isobutene; less than 0.5 weight percent total in other embodiments; less than 0.1 weight percent total in other embodiments; and less than 500 ppm total in yet other embodiments.

The overheads fraction, including the isobutene and isobutane may also contain some unreacted 1-butene. In some embodiments, the overheads fraction may contain less than 1000 ppm 1-butene; less than 500 ppm in other embodiments; less than 250 ppm in other embodiments; less than 100 ppm in other embodiments; and less than 50 ppm in yet other embodiments. In other embodiments, the overhead fraction may be substantially pure isobutene.

The overhead fraction may then be reacted to form desired dimerization and/or oligomerization reaction products, such as C8 to C16 hydrocarbons, among others, according to embodiments herein.

Whether or not pre-processing of the feed to produce a desired olefin fraction, such as a purified isobutene feed, processes disclosed herein may include any number of reactors, including catalytic distillation reactor systems, both up-flow and down-flow. Use of catalytic distillation reactor systems may prevent foulants and heavy catalyst poisons in the feed from building up within the reaction zone(s). In addition, clean reflux may continuously wash the catalytic distillation structure in the reaction zone. These factors combine to provide a long catalyst life. The heat of reaction evaporates liquid and the resulting vapor is condensed in the overhead condenser to provide additional reflux.

Other reactors useful in embodiments disclosed herein may include traditional fixed bed reactors, boiling point reactors, and pulsed flow reactors, where the reactant flow and product flow may be co-current or counter-current. Boiling point and pulsed flow reactors may also provide for a continuous washing of the catalyst in addition to capturing at least a portion of the heat of reaction through evaporation, allowing for an improved reactor temperature profile as compared to conventional fixed bed reactors. Reactors useful in embodiments disclosed herein may be used as a stand-alone reactor or may be used in combination with one or more reactors of the same or different type.

Any type of reactor may be used to carry out the reactions described herein. The examples of reactors suitable for carrying out the reactions involving olefin and/or isoolefin reactions according to embodiments herein may include distillation column reactors, divided wall distillation column reactors, traditional tubular fixed bed reactors, bubble column reactors, slurry reactors equipped with or without a distillation column, pulsed flow reactors, catalytic distillation columns wherein slurry solid catalysts flow down the column, or any combination of these reactors. Multiple reactor systems useful in embodiments disclosed herein may include multiple reactors in series and/or multiple reactors in parallel. A person of ordinary skill in the art would recognize that other types of reactors may also be used.

The reactors useful in embodiments disclosed herein may include any physical devices or a combination of two or more devices, including reactors and reactor systems as described above. The reactor(s) may have various internal devices for vapor-liquid separation and vapor/liquid traffic. Reaction zones within the reactor(s) may include "wettable" structure and/or packing. Wettable structure and packing useful in embodiments disclosed herein may include various distillation structures and packing materials, which may be catalytic or non-catalytic. Suitable wettable structure and packing may include, for example, random or dumped distillation packings which are: catalytically inert dumped packings that contain higher void fraction and maintain a relatively large surface area, such as, Berl Saddles (Ceramic), Raschig Rings (Ceramic), Raschig Rings (Steel), Pall rings (Metal), Pall rings (Plastic, e.g. polypropylene) and the like. Monoliths, which are structures containing multiple, independent, vertical channels and may be constructed of various materials such as plastic, ceramic, or metals, in which the channels are typically square, are also suitable wettable structures. Other geometries could also be used.

Other materials that promote the distribution of liquid and vapors may also be used, including mist eliminators, demisters, or other wire or multi-filament type structure. Such multi-filament structures may include one or more of fiberglass, steel, Teflon, polypropylene, polyethylene, polyvinylidenedifluoride (PVDF), polyester, or other various materials, which may be knitted (or co-knit, where more than one type of filament or wire structure is used), woven, non-woven, or any other type of multi-filament structure. Structures including multifilament wires as typically used in demister services, structures including an element of woven fiberglass cloth, and high surface area stainless steel structured packings are preferred.

Reactor systems according to embodiments disclosed herein may include one or multiple reaction zones. In some embodiments, one or multiple fixed bed reactors may be used to perform an initial conversion of the olefins and/or isoolefins, which may be followed by a catalytic distillation column to supplement the conversion and separate the heavier reaction products from the unreacted feed components.

The primary oligomer products are dimers and trimers of the olefins and/or isoolefins. For example, isobutene may be oligomerized to form a $C_8$ or $C_{12}$ tertiary olefin. In some embodiments, the C4 oligomers have 8 to 16 carbon atoms and correspond to oligomers prepared from $C_4$ olefins. Reactions herein may be configured to increase the selectivity toward the C8 dimer. Likewise, when a C5 feedstock is used, the oligomer products may be C10, C15, or C20 olefins, and when a mixed feedstock is used, the codimers and cotrimers may range from C9 to C19, for example.

Oxygen-containing moderators may be used to influence the selectivity of the oligomerization reaction to the dimer product. Oxygen-containing moderators useful in embodiments disclosed herein may include water as well as tertiary alcohols and ethers. For example, the oxygen-containing moderator may include at least one of: water, methanol, ethanol, propanol, isopropanol, butanol, isobutanol, tertiary butyl alcohol, methyl tertiary butyl ether, and ethyl tertiary butyl ether. Mixtures of the alcohols or one or more alcohols and water may also be used. In some embodiments, the weight ratio of mixed C4s to oxygenates may be from 5:1 to 2:1.

Oligomerization reactions carried out in the presence of the oxygen-containing moderators may concurrently produce oligomers, such as dimers and trimers of the isoolefins or n-olefins, and various oxygen-containing byproducts resulting from reaction of a moderator with an olefin, an isoolefin or an isoolefin oligomer, such as a dimer or trimer. For example, the oxygenated oligomerization byproducts may include $C_5$-$C_{16}$ ethers and $C_5$-$C_{12}$ alcohols. In some embodiments, a C4 olefin may react with a moderator to form secondary ethers, such as methyl tert-butyl ether or methyl sec-butyl ether, which may be undesirable.

The oligomerization of the olefins and isoolefins may be carried out in a partial liquid phase in the presence of an acid cation resin catalyst either in straight pass type reaction or in a catalytic distillation reaction where there is both a vapor and liquid phase and a concurrent reaction/fractionation. Catalysts used in oligomerization reactors according to embodiments herein may include acid resins, such as AMBERLYST 15 (available from DuPont) or related oleum derived resins and may include phosphoric acid derived catalysts, such as those known to the industry as SPA (solid phosphoric acid) catalysts. Sulfonic acid catalysts may also be used, such as a macroporous, strongly acid cationic, sulfonic acid catalysts based on polystyrene divinylbenzene sulfonate, among other catalysts.

In some embodiments, the resin catalysts may be tailored to have a low reactivity with oxygen-containing moderators. For example, appropriate crosslinking and acid functionality of the acid resin catalyst may provide for decreased reactivity with the oxygen-containing moderators, thus providing for reduced purification needs downstream to address the oxygenate byproducts that may result with higher oxygenate-reactive catalysts. In prior C4 dimerization schemes, fixed bed reactions are staged to increase the selectivity toward the C8 dimer, including intermediate separations between reactors to minimize reaction of the C8 dimer to produce trimer in subsequent reactors. The present inventors have found that through proper dimerization reaction conditions and appropriate use of a selectivator or moderator in each reactor, the need for an intermediate separator, such as a debutanizer, may be minimal or unnecessary while still achieving a high olefin and/or isoolefin conversion. Thus, in some embodiments, the effluent from a first reactor may be fed directly to a second reactor without intermediate componential separations.

Following reaction in upstream reactors, such as fixed bed reactors, the effluent from the last reactor may be fed to a catalytic distillation column reactor to separate the reaction products while targeting further conversion of the isobutene or other C4 to C5 olefins. In some embodiments, the catalytic distillation column reactor may be used to target complete conversion of the light olefins and isoolefins. Embodiments herein contemplate continued dimerization in the catalytic distillation column reactor.

The resulting dimers may be used, for example, as a raw material for the production of various chemicals, such as herbicides and pesticides. In other embodiments, the dimer may be fed to an alkylation system, where the dimer may dissociate into constituent olefins and react with an alkane to produce an alkylate in the gasoline-boiling range. The dimers may also be hydrogenated to form gasoline-range hydrocarbons, such as iso-octane, iso-nonane, and other hydrocarbons. In yet other embodiments, the dimer-containing stream may be used as a gasoline-range hydrocarbon blendstock without hydrogenation or alkylation.

Operating conditions within catalytic distillation reactor systems for dimerizing isoolefins as described above may include temperatures and pressures sufficient for a) recovery of the unreacted C4 and/or C5 hydrocarbons, water, and other light components as an overhead vapor fraction, b) the desired reactivity of the isoolefins over the catalyst, and c) recovery of the dimer as a bottoms liquid fraction. The temperature within the reaction zone may thus be intimately linked to the pressure, the combination of which provides for boiling of the olefin and/or isoolefin and water within the reaction zone(s). Higher temperatures may be required for a C5 feedstock as compared to a C4 feedstock, as well as in portions of the column below the reaction zone, thus providing for the separation of the dimer from the unreacted feed compounds.

The temperature in the column is determined by the boiling point of the liquid mixture present at any given pressure. The temperature in the lower portions of the column will reflect the constitution of the material in that portion of the column, which will be higher than the overhead; that is, at constant pressure a change in the temperature indicates a change in the composition in the column. To change the temperature, the pressure in the column may be changed. Temperature control in the reaction zone is thus controlled by the pressure with the addition of heat (the reactions being exothermic) only causing more boil up. By increasing the pressure the temperature is increased, and vice versa. Even though a distillation column reactor is used, some of the olefins and/or isoolefin may be unconverted and may exit the column with the overheads.

The dimers, oligomers, and any ether byproducts (depending on the alcohol used), being the highest boiling materials, are removed from the distillation column reactor as a bottoms fraction. The overheads fraction may contain moderator, unreacted olefin and/or isoolefin, and any light inerts contained in the feed, such as butanes and pentanes. In some embodiments the moderator may be recycled to the first reactor in a closed loop fashion thereby allowing for a single, initial charge of moderator without the need for continuous oxygenate feed. In a similar manner, diluent may also be charged and recirculated in a closed loop fashion; for example, in embodiments where a purified isobutene feed is used, the n-butane diluent may be fed in a single, initial charge and recycled to the first reactor with, or separately from, any moderator.

Referring now to FIG. 1, a simplified process flow diagram of a system for the oligomerization (dimerization) of olefins and/or isoolefins according to embodiments disclosed herein is illustrated. While described below with respect to a mixed C4 feed, the system may similarly be used for the processing of a mixed C4/C5 feed or a mixed C5 feed.

Figure 3:
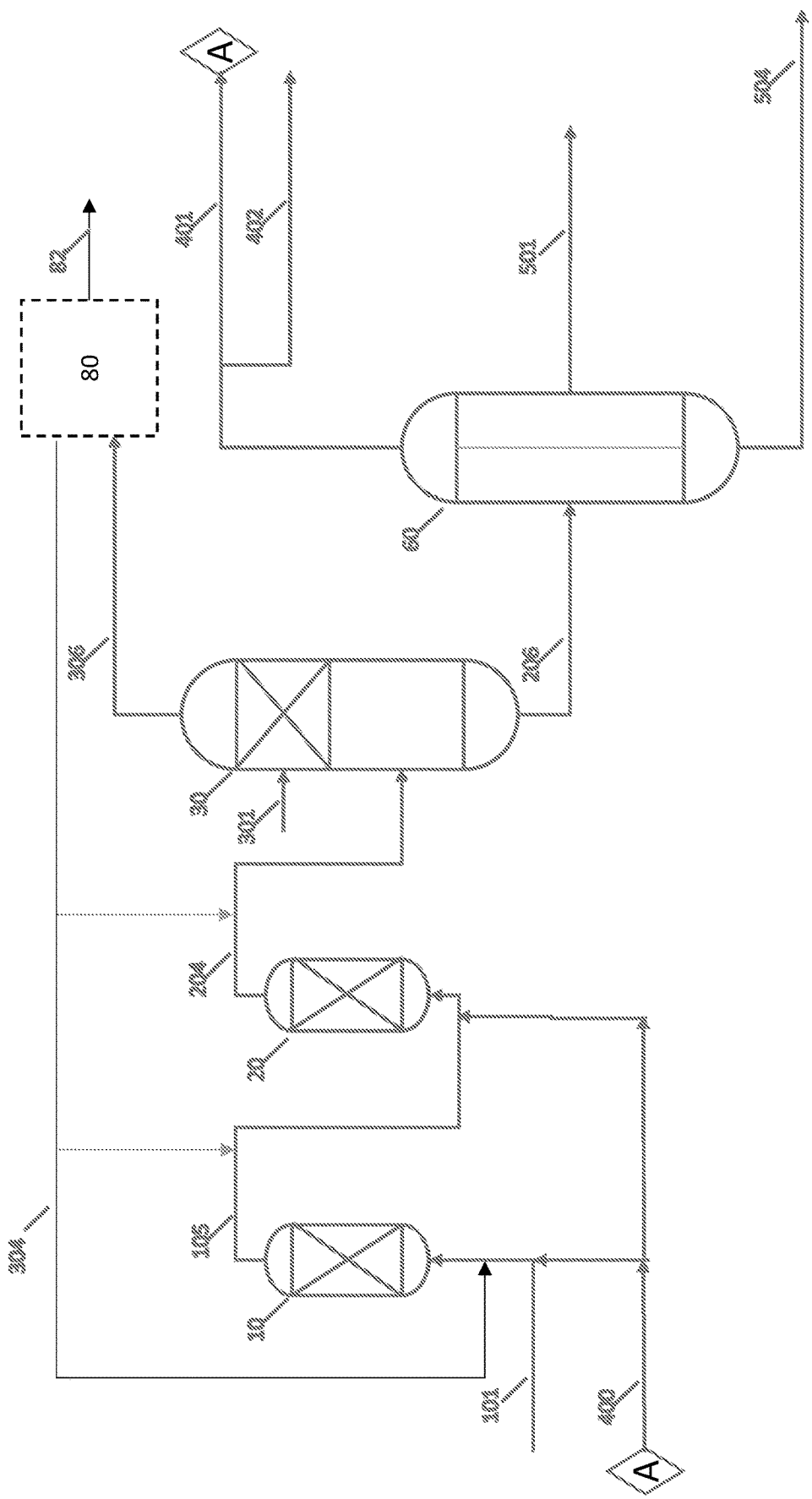
FIG. 3 is a simplified process flow diagram of a system for dimerization and/or oligomerization of olefins according to embodiments herein.

A hydrocarbon feed, such as a Raffinate (RAFF-1) from a butadiene separation process, containing isoolefins, such as isobutene, and one or more of isobutane, 1-butene, butadiene, n-butane, and 2-butene, may be fed via flow line 101 to a reactor 10, such as a fixed bed reaction system containing a catalyst suitable for oligomerization reactions. In some embodiments, the butadiene in the feedstock may be limited to less than 3000 ppm via an upstream process such as a hydrogenation process. A reaction moderator, such as one or multiple alcohols, may also be fed to reactor 10 via flow line 400. Alternatively, and/or additionally, additional moderator may be fed to reactor 10 via flow line 304; such additional moderator may come from a downstream or upstream alcohol recovery system, such as illustrated in FIG. 3, for example.

In reactor 10, the isobutene reacts in the presence of the catalyst contained in the reaction zone to convert a portion of the isobutene and n-olefins to oligomers, including dimers of isobutene. The effluent 105 from reactor 10 may then be combined with additional reaction moderator (e.g., oxygenates) and fed to reactor 20, also containing a catalyst suitable for oligomerization reactions. In reactor 20, the isobutene reacts in the presence of the catalyst contained in the reaction zone to convert a portion of the isobutene to form additional oligomers, including dimers of isobutene, in addition to those produced in reactor 10. Feeding effluent 105 to reactor 20 may, in some embodiments, be done without the step of an intermediate separator.

The effluent 204 from reactor 20 may then be fed to a catalytic distillation column 30. If necessary or desired, additional moderator 301 may be fed directly to catalytic distillation column 30. The feed of the effluent from reactor 30 may be introduced to the catalytic distillation column below the reaction zone containing a catalyst suitable for oligomerization. The heavier reaction products may distill downward, and the isobutene and lighter components upward into the reaction zone, where the isobutene and/or other olefins reacts in the presence of the catalyst contained in the reaction zone to convert a portion of the isobutene to oligomers, including dimers of isobutene.

The overhead distillate 306 from catalytic distillation reactor 30 may include unreacted C4s, such as n-butane, 2-butene, 1-butene, and isobutene, as well as unreacted alcohols, such as methanol. In some embodiments, the overhead distillate 306 may be sent to one or more downstream processes such as an alcohol extraction and recovery, alkylation, isomerization, or metathesis processes.

As a side reaction, the moderator may react with a portion of at least one of the isoolefin and any 1-butene present in the reaction zones to form oxygenated oligomerization byproducts, such as methyl sec-butyl ether. Concurrent with the oligomerization reactions, the oligomers, including dimers and trimers, as well as heavy reaction byproducts distill downward and may be recovered as a bottoms fraction via a flow line 206, and the isobutane and any unreacted alcohol, isobutene and 1-butene, if present and unreacted, may distill upward and be recovered via an overhead flow line 306.

The catalytic distillation column bottoms 206 may include dimers and trimers produced via reaction in reactors 10, 20, 30, and may be used as a raw material for various downstream processes. For example, a resulting dimer fraction may be used as a raw material for the production of various chemicals, such as herbicides and pesticides. In other embodiments, the dimers may be fed to an alkylation system, where the dimers may dissociate into constituent olefins and react with an alkane to produce an alkylate in the gasoline-boiling range. The dimer may also be hydrogenated to form gasoline-range hydrocarbons, such as octane, nonane, and other hydrocarbons. In yet other embodiments, the dimer containing stream may be used as a gasoline-range hydrocarbon blendstock without hydrogenation or alkylation.

Alternatively, the bottoms 206 may then be further separated, if desired, such as in one or more distillation columns, such as fractionation columns 40 and 50, as illustrated in FIG. 1. The catalytic distillation column bottoms 206, which includes dimers and trimers, as well as higher boiling oxygenates, may be sent to a first fractionation column 40. The overheard product stream 401, which may include any unreacted feed components, such as C4 or C5 olefins and isoolefins, as well as inerts such as butanes or isobutanes, and light oxygenates such as methanol, as well as any lighter ethers formed, such as MTBE and MSBE, may be recycled to reactors 10 and/or 20 as the oxygenate moderator 400. A portion of the overhead product stream 401 may also be purged by flow line 402, or may be used as a fuel blend.

The bottoms product stream 402, from column 40, which may include the dimers and trimers of isobutene, may be fed directly as export grade product, used as a fuel blend, fed to a downstream hydrogenation process, or further fractionated, such as in column 50. Column 50 may separate the bottoms product 402 into an overhead dimers (isooctene) stream 501, and a C12+ fraction 504, which includes trimers and higher oligomers of the olefins and/or isoolefins.

FIG. 1 is illustrated with a separation system including two distillation columns producing the dimer as an overhead product 501. In other embodiments, as illustrated in FIG. 2, a single divided wall distillation column 60 may be used to separate catalytic distillation column 30 bottoms product stream 206 into overhead product stream 401, dimer stream 501, and heavies stream 504.

Figure 2:
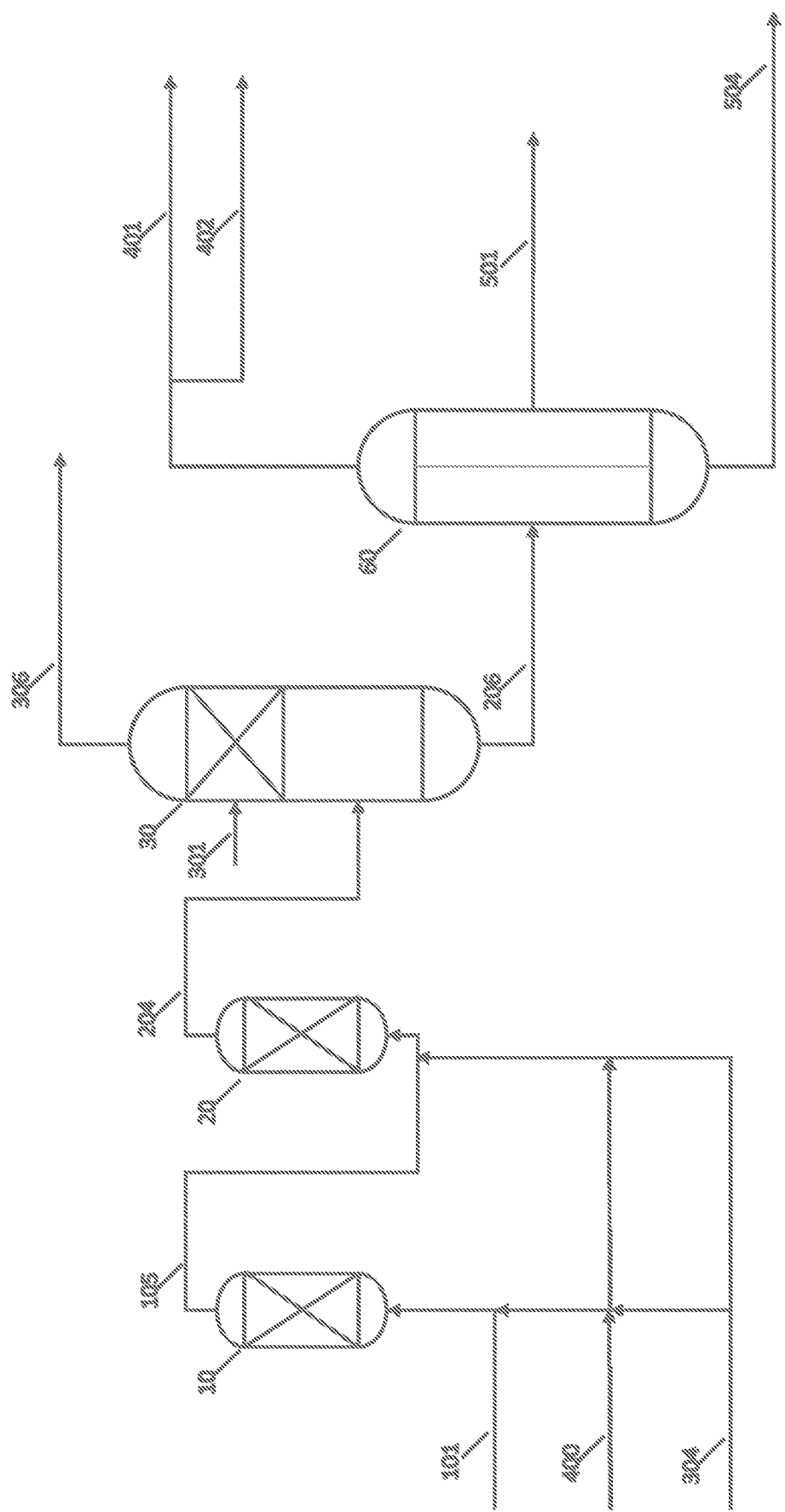
FIG. 2 is a simplified process flow diagram of a system for dimerization and/or oligomerization of olefins according to embodiments herein.

FIG. 3 illustrates a process similar to the system of FIG. 2, including an alcohol recovery system 80, which may be used to separate overhead product 306 from the distillation column reactor into a recycle alcohol stream 304 and a hydrocarbon fraction 82 including unreacted C4-C5 olefins, unreacted C4-C5 isoolefins, and inerts.

As noted above, embodiments herein may utilize an acidic catalyst having a very high selectivity for oligomerization. The lower oxygenate moderator conversion to heavy oxygenate byproducts may provide for advantageous processing. For example, having little or no heavy oxygenates, such as MTBE, MSBE, and heavier oxygenate byproducts, may allow for the dimer and oligomer products to be used directly, without further componential separations following recovery in the separation section, whether it be in a divided wall column or multiple distillation columns.

In some embodiments, for example, methanol may be used as an oxygenate modifier. When used, the methanol may react to form MTBE and MSBE, for example, as well as the corresponding amylene ethers. The methanol may be recovered in the overheads from the catalytic distillation reactor, and the overheads may be fed to an alcohol recovery zone. As water may be used to separate and recover the methanol, methanol recycled to the reactors may contain some water.

In other embodiments, the n-butanes used as a diluent may be recycled together, or separately, from the methanol recycled to the reactors.

Ethanol, when used, may be recovered in both the overheads and bottoms from the catalytic distillation column. Accordingly, an alcohol recovery section may be desirable when ethanol is used.

In other embodiments using methanol or ethanol, it has been found that it is possible to avoid the need for an alcohol recovery section altogether. Rather, the alcohol moderator and any added diluent, such as n-butane, isobutane, n-pentane, or isopentane, may be circulated through the system from the first reactor through to the catalytic distillation reactor and then back to the first reactor in a "closed loop" fashion for providing the diluent and moderator to the reactors.

For example, in embodiments where the feed includes a high purity isobutene, a high purity isoamylene, or mixtures thereof, such as feeds with greater than >99.5, >99.8, or greater than 99.9 wt % isobutene or isoamylene, the n-butane or n-pentane diluent may be charged once and recycled in closed loop. If needed, an occasional make-up charge of diluent may be added.

Figure 4:
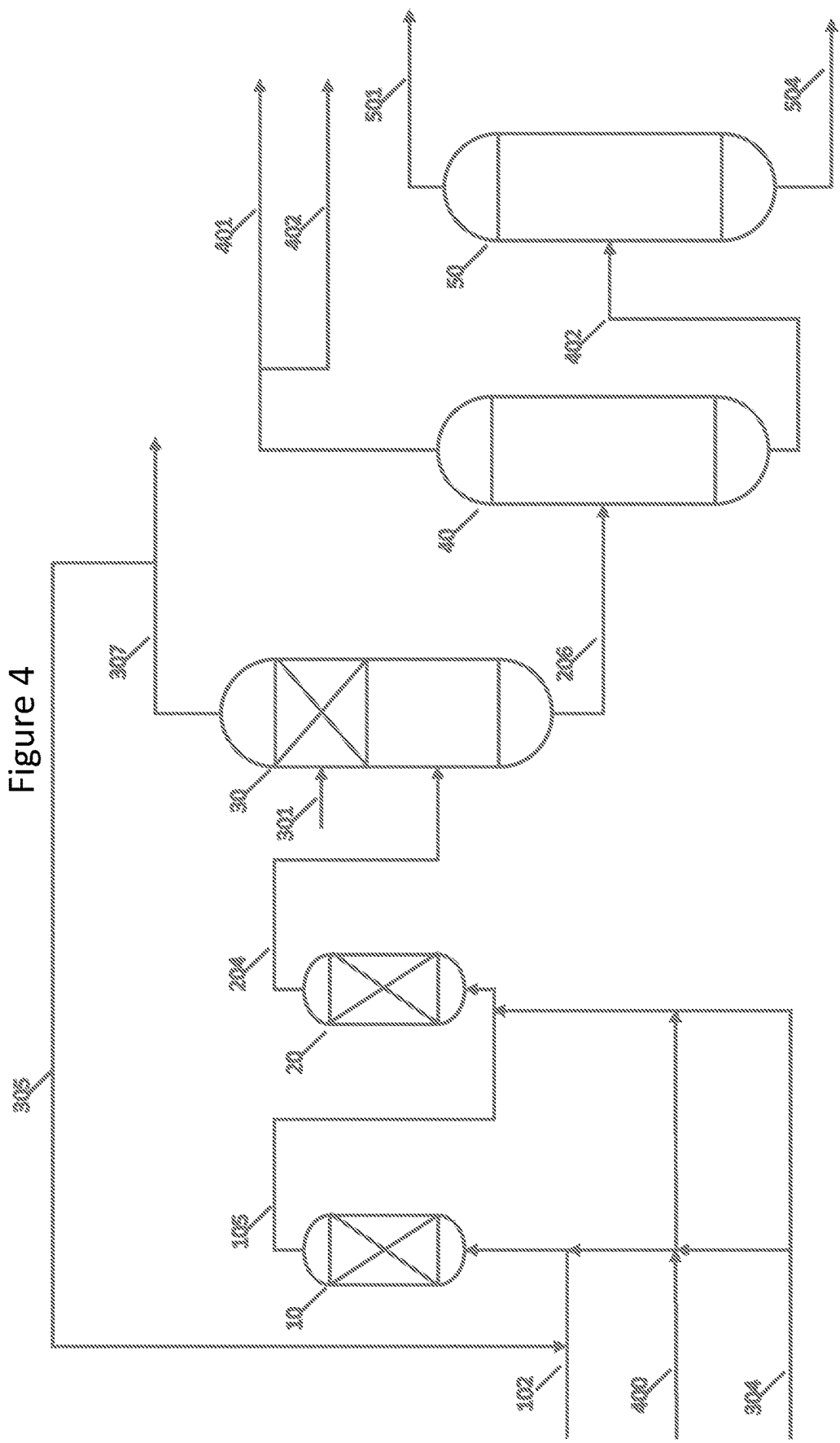
FIG. 4 is a simplified process flow diagram of a system for dimerization and/or oligomerization of olefins according to embodiments herein.

FIG. 4 illustrates a process similar to the system of FIG. 1. In one or more embodiments as illustrated in FIG. 4, the feedstock 102 may be a pure isobutene stream with butanes, including n-butanes, isobutane, or both, as a diluent. In such embodiments, a portion of overhead product 307 from the distillation column reactor 30 may be recycled as stream 305 and mixed with the hydrocarbon feed 102 containing isobutene. Stream 307 may also be fully, or partially, recycled and mixed with hydrocarbon feed 102 containing isobutene. In embodiments where the feed is essentially pure isobutene with butanes as a diluent, the overhead product 307 is expected to be butanes and light alcohols such as methanol and ethanol. In other embodiments, the feedstock 102 may be pure isobutene with butanes as a diluent. In such embodiments, the system may be initially charged with a predetermined amount of butanes, and the butanes economy would be essentially closed loop.

Accordingly, embodiments where a pure or high purity (polymerization grade or better) isobutene stream 102 is used, the process may proceed as follows.

A hydrocarbon feed containing pure isobutene, may be fed via flow line 102 to a reactor 10, such as a fixed bed reaction system containing a catalyst suitable for oligomerization reactions. A reaction moderator, such as one or multiple alcohols, may also be fed to reactor 10 via flow line 400. Alternatively, and/or additionally, additional moderator may be fed to reactor 10 via flow line 304; such additional moderator may come from a downstream or upstream alcohol recovery system or the overhead splitter 60, such as illustrated in FIG. 3, for example.

In reactor 10, the isobutene reacts in the presence of the catalyst contained in the reaction zone to convert a portion of the isobutene to oligomers, including dimers of isobutene. The effluent 105 from reactor 10 may then be combined with additional reaction moderator (e.g., oxygenates) and fed to reactor 20, also containing a catalyst suitable for oligomerization reactions. In reactor 20, the isobutene reacts in the presence of the catalyst contained in the reaction zone to convert a portion of the isobutene to form additional oligomers, including dimers of isobutene, in addition to those produced in reactor 10. Feeding effluent 105 to reactor 20 may, in some embodiments, be done without the step of an intermediate separator.

The effluent 204 from reactor 20 may then be fed to a catalytic distillation column 30. If necessary or desired, additional moderator 301 may be fed directly to catalytic distillation column 30. The feed of the effluent from reactor 30 may be introduced to the catalytic distillation column below the reaction zone containing a catalyst suitable for oligomerization. The heavier reaction products may distill downward, and the isobutene and lighter components, such as unreacted alcohol upward into the reaction zone, where the isobutene reacts in the presence of the catalyst contained in the reaction zone to convert a portion of the isobutene to oligomers, including dimers of isobutene.

The overhead distillate 307 from catalytic distillation reactor 30 may include unreacted C4s, such as butanes, and isobutene, as well as unreacted alcohols, such as methanol and ethanol, and may be recycled to feedstock 102.

As a side reaction, the moderator may react with a portion of the isobutene in the reaction zones to form oxygenated oligomerization byproducts, such as methyl sec-butyl ether. Concurrent with the oligomerization reactions, the oligomers, including dimers and trimers, as well as heavy reaction byproducts distill downward and may be recovered as a bottoms fraction via a flow line 206, and the n-butanes and any unreacted alcohol, isobutene, if present and unreacted, may distill upward and be recovered via an overhead flow line 307.

The catalytic distillation column bottoms 206 may include dimers and trimers produced via reaction in reactors 10, 20, 30, and may be used as a raw material for various downstream processes. For example, a resulting dimer fraction may be used as a raw material for the production of various chemicals, such as herbicides and pesticides. In other embodiments, the dimers may be fed to an alkylation system, where the dimers may dissociate into constituent olefins and react with an alkane to produce an alkylate in the gasoline-boiling range. The dimer may also be hydrogenated to form gasoline-range hydrocarbons, such as octane, nonane, and other hydrocarbons. In yet other embodiments, the dimer containing stream may be used as a gasoline-range hydrocarbon blendstock without hydrogenation or alkylation.

Alternatively, the bottoms 206 may then be further separated, if desired, such as in one or more distillation columns, such as fractionation columns 40 and 50, as illustrated in FIG. 1.

Figure 5:
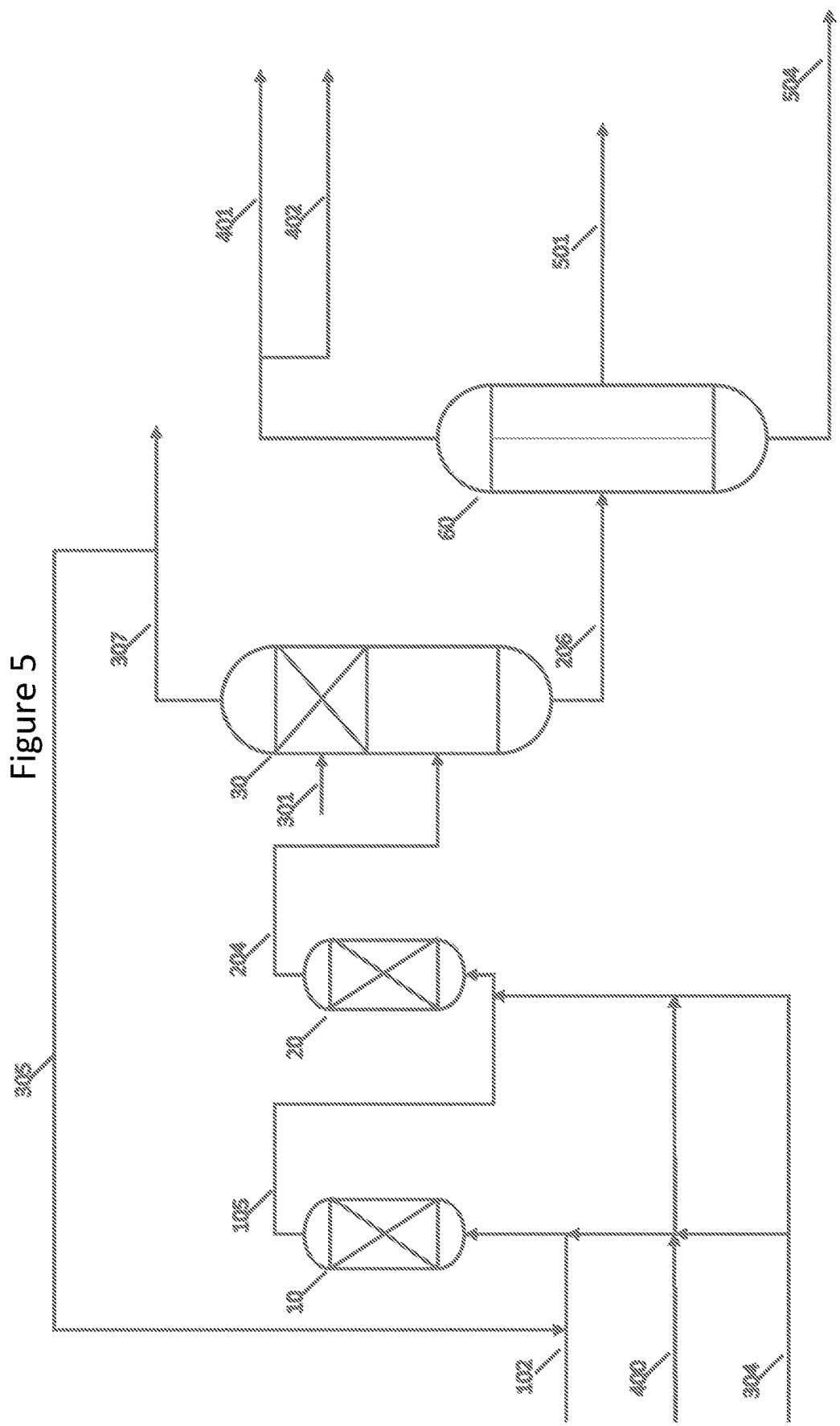
FIG. 5 is a simplified process flow diagram of a system for dimerization and/or oligomerization of olefins according to embodiments herein.

In other embodiments, as illustrated in FIG. 5, a single divided wall distillation column 60 may be used to separate catalytic distillation column 30 bottoms product stream 206 into overhead product stream 401, dimer stream 501, and heavies stream 504.

While described above with respect to closed loop butane diluent, embodiments processing isopentane may similarly benefit from such a closed loop system where the diluent and moderator may be recovered and recycled without the need for an alcohol recovery system.

As noted above, the dimerization and oligomerization reactions are exothermic. If needed, an interstage cooler may be provided to control or moderate a temperature of the effluent from reactor 10 being fed to reactor 20.

While the system of FIGS. 1-5 are illustrated as including two fixed bed reactors, more or fewer rectors may be used. In such embodiments, the feed of oxygenates and/or alcohols may be staged so as to achieve the desired selectivity in the dimerization and/or etherification reactions.

In some embodiments, the oxygenate reaction moderator may be or may include tertiary butyl alcohol. In some embodiments, recycle methanol may contain water, as noted above, which may react with isobutene, for example, to form tertiary butyl alcohol. Tertiary butyl alcohol has been found to form an azeotrope with C8 olefins, and may thus be recovered with the dimer product stream. Use of a C5 olefin in the feed has been found to help break the azeotrope, and may allow a cleaner recovery of the dimer products when using a side-draw, as illustrated in FIGS. 2 and 3.

In embodiments with a high selectivity/low oxygenate reactivity catalyst, it has been found that tertiary butyl alcohol may have little to no reactivity with the olefins and isoolefins. In such embodiments, an alcohol recovery section may be omitted from the process, as the oxygenate recovered in the overheads from the divided wall column may be recycled to the reactors for continued use as a reaction moderator.

Ethanol, when used, may be recovered in both the overheads and bottoms from the catalytic distillation column. Accordingly, an alcohol recovery section may be desirable when ethanol is used.

Propanol and isopropanol have also been found to have little to no reactivity over the high selectivity/low oxygenate reactivity catalyst. In such embodiments, the C3 alcohols may be recovered in the bottoms of the catalytic distillation reactor and may then be recovered in the overheads of the first distillation column or in the overheads of the divided wall distillation column. In such embodiments, the alcohol may be recovered in the overheads of the divided wall distillation column and may be recycled to the reactors for continued use as a reaction moderator.

Where a heavier moderator (propanol, isopropanol, tertiary butyl alcohol for example) is used, the overheads from the catalytic distillation column may include only the unreacted light hydrocarbon feed components. The recovery of a C4 stream free of oxygenates may allow the catalytic distillation overhead stream to be recovered for use in downstream processes with little or no additional processing prior to use, such as in an alkylation zone to convert the isobutane to octanes, among other possible downstream uses that may be readily envisaged.

As described above, in some embodiments, catalysts used in the oligomerization reaction zones may be selected to have low oxygenate reactivity, producing less oxygenate byproducts. Alternatively, or additionally, the oxygenate moderator used may have low reactivity over the catalyst selected. Advantageously, systems and processes herein may advantageously use C3 and heavier alcohols as reaction moderators, thereby minimizing or eliminating the need for alcohol separations on the catalytic distillation overheads stream.

As described above, C4 olefins comprised of isobutene, butene-1 and butene-2 from a hydrocarbon feedstock are mixed with a fraction of C1 to C4 alcohols and/or water. The controlled oligomerization process can be carried out using any of the C1 to C4 alcohols and water or a combination of alcohols and water. The mixed C4s and alcohol is then sent to a fixed bed reactor containing the oligomerization acidic catalyst wherein the controlled oligomerization reactions proceed to form C8, C12 and C16 olefins. To moderate the reactions and improve selectivity to form C8 olefins, C1 to C4 alcohols and/or water act as modulators or selectivators. Depending on the C4 olefin conversion, one or two reactors are operated in series to improve the overall butylenes conversion. The effluent of the oligomerization reactor feeds the Catalytic Distillation column wherein a catalytic section containing the oligomerization catalyst is located. Depending on the type of alcohol, the recovery of the alcohol can be at the top or the bottom of the catalytic distillation. The bottom of the catalytic distillation is then sent to a fractionation step comprised of a Dividing Wall Column to separate the alcohol, oxygenates and water from the C8, C12 and C16 olefins. The dividing wall in the column can be off-center or in the middle depending on the amount of C12 and C16 olefins produced. The overhead of the Dividing Wall Column comprised mostly of the recovered alcohol and some oxygenates is then sent back to the reactors and the catalytic distillation to control the oligomerization reaction. A side cut of high purity C8 olefins is taken from the right side of the dividing wall column; for example, the side cut may contain greater than 90 wt % C8 olefins in some embodiments, greater than 95 wt % C8 olefins in other embodiments, and greater than 98 wt % C8 olefins in yet other embodiments. While described above largely with respect to a C4 cut, processes herein using C5 or mixed C4/C5 feeds may likewise be operated to produce a side cut having similar dimer purities. Depending on the type of alcohol, if the alcohol is light that it fractionates from the top of the Catalytic Distillation column, it may be recovered by countercurrent washing with water followed by fractionation to further separate the alcohol. The recovered alcohol from the fractionation step is then recycled to the reactors and the catalytic distillation column. Makeup alcohol is fed as needed.

One of the advantages over the prior art is the very minimal production of ethers (like MTBE, MSBE, ETBE, ESBE) which gives the plant better flexibility in the requirement of the oxygenates. Depending on the plant requirements, the process can be tailor fitted with the right alcohol. Further, use of a divided wall distillation column in the subsequent heavier fractionation step may also reduce equipment count and plot space compared to a conventional tower sequence.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the dimerization of isoolefins, the process comprising:
    feeding an oxygenate reaction modifier and a hydrocarbon feed to a fixed bed reactor containing an oligomerization catalyst, the hydrocarbon feed comprising isobutene and a secondary feed comprising butanes;
    reacting isobutene in the fixed bed reactor at oligomerization conditions to form a reaction effluent comprising the oxygenate reaction modifier, isobutene dimers, unreacted isobutene, any oxygenate reaction byproducts formed, as well as butanes;
    without componential separation, feeding the reaction effluent to a second fixed bed reactor containing an oligomerization catalyst;
    reacting the unreacted isobutene in the second fixed bed reactor at oligomerization conditions to form additional isobutene dimers, recovering a second reaction effluent comprising the oxygenate reaction modifier, isobutene dimers, any oxygenate reaction byproducts formed, as well as butanes;
    without componential separation, feeding the second reaction effluent to a catalytic distillation reactor having a reactive distillation zone comprising an oligomerization catalyst;
    concurrently within the catalytic distillation reactor:
        reacting unreacted isobutene in the second reaction effluent to form additional isobutene dimers;
        separating the dimers and the oxygenate reaction byproducts, recovered as a bottoms fraction, from the isobutane and n-butane, and any unreacted isobutene, recovered as an overheads fraction; and
    recycling the overheads fraction to the hydrocarbon feed;
    wherein the bottoms fraction further comprises the oxygenate reaction modifier and isobutene trimers, the process further comprising separating the bottoms fraction in a divided wall distillation column to recover an overheads fraction, a side draw fraction comprising the isobutene dimers, and a bottoms fraction comprising the isobutene trimers; and
    wherein the side draw fraction comprises greater than 95 wt % isobutene dimers.

2. The process of claim 1, wherein the oligomerization catalyst contained in each of the fixed bed reactor, second fixed bed reactor, and reactive distillation zone comprises a sulfonic acid catalyst.

3. The process of claim 1, wherein the oxygenate reaction modifier is selected from the group consisting of methanol and ethanol, and mixtures thereof.

4. The process of claim 1, wherein the secondary feed is fed to the reactor initially and the n-butane is recycled in a closed loop cycle.

5. A process for the dimerization of isoolefins, the process comprising:
    feeding an oxygenate reaction modifier and a hydrocarbon feed to a fixed bed reactor containing an oligomerization catalyst, the hydrocarbon feed consisting of isoolefins and n-paraffins;
    reacting isoolefins in the fixed bed reactor at oligomerization conditions to form a reaction effluent comprising the oxygenate reaction modifier, isoolefin dimers, unreacted isoolefin, any oxygenate reaction byproducts formed, as well as n-paraffins;

without componential separation, feeding the reaction effluent to a second fixed bed reactor containing an oligomerization catalyst;
reacting the unreacted isoolefins in the second fixed bed reactor at oligomerization conditions to form additional isoolefin dimers, recovering a second reaction effluent comprising the oxygenate reaction modifier, isoolefin dimers, any oxygenate reaction byproducts formed, as well as n-paraffins;
without componential separation, feeding the second reaction effluent to a catalytic distillation reactor having a reactive distillation zone comprising an oligomerization catalyst;
concurrently within the catalytic distillation reactor:
reacting unreacted isoolefins in the second reaction effluent to form additional isoolefin dimers;
separating the dimers and the oxygenate reaction byproducts, recovered as a bottoms fraction, from the n-paraffin, and any unreacted isoolefin, recovered as an overheads fraction;
recycling the overheads fraction to the hydrocarbon feed;
wherein the bottoms fraction further comprises the oxygenate reaction modifier and isoolefin trimers, the process further comprising separating the bottoms fraction in a divided wall distillation column to recover an overheads fraction, a side draw fraction comprising the isoolefin dimers, and a bottoms fraction comprising the isoolefin trimers; and
wherein the side draw fraction comprises greater than 95 wt % isoolefin dimers.

6. The process of claim 5, wherein the oligomerization catalyst contained in each of the fixed bed reactor, second fixed bed reactor, and reactive distillation zone comprises a sulfonic acid catalyst.

7. The process of claim 5, wherein the oxygenate reaction modifier is selected from the group consisting of methanol and ethanol, and mixtures thereof.

8. The process of claim 5, wherein one or both of the bottoms fraction from the divided wall distillation column and the overheads fraction from the divided wall distillation column comprise oxygenated byproducts or comprise the oxygenate reaction modifier, the process further comprising:
recovering the oxygenate reaction modifier or oxygenated byproducts from one or both of the bottoms fraction from the divided wall distillation column and the overheads fraction from the divided wall distillation column; and
recycling the recovered oxygenate reaction modifier or oxygenated byproducts to the fixed bed reactor, the second fixed bed reactor, the catalytic distillation reactor, or a combination thereof.

9. A process for the dimerization of isoolefins, the process comprising:
feeding an oxygenate reaction modifier and a hydrocarbon feed to a fixed bed reactor containing an oligomerization catalyst, the hydrocarbon feed comprising isobutene and a secondary feed comprising butanes;
reacting isobutene in the fixed bed reactor at oligomerization conditions to form a reaction effluent comprising the oxygenate reaction modifier, isobutene dimers, unreacted isobutene, any oxygenate reaction byproducts formed, as well as butanes;
without componential separation, feeding the reaction effluent to a second fixed bed reactor containing an oligomerization catalyst;
reacting the unreacted isobutene in the second fixed bed reactor at oligomerization conditions to form additional isobutene dimers, recovering a second reaction effluent comprising oxygenate reaction modifier, isobutene dimers, any oxygenate reaction byproducts formed, as well butanes;
without componential separation, feeding the second reaction effluent to a catalytic distillation reactor having a reactive distillation zone comprising an oligomerization catalyst;
concurrently within the catalytic distillation reactor:
reacting unreacted isobutene in the second reaction effluent to form additional isobutene dimers;
separating the dimers and the oxygenate reaction byproducts, recovered as a bottoms fraction, from the isobutane and n-butane, and any unreacted isobutene, recovered as an overheads fraction; and
recycling the overheads fraction to the hydrocarbon feed;
wherein the bottoms fraction further comprises the oxygenate reaction modifier and isobutene trimers, the process further comprising separating the bottoms fraction in a divided wall distillation column to recover an overheads fraction, a side draw fraction comprising the isobutene dimers, and a bottoms fraction comprising the isobutene trimers; and
wherein one or both of the bottoms fraction from the divided wall distillation column and the overheads fraction from the divided wall distillation column comprise oxygenated byproducts or comprise the oxygenate reaction modifier, the process further comprising:
recovering the oxygenate reaction modifier or oxygenated byproducts from one or both of the bottoms fraction from the divided wall distillation column and the overheads fraction from the divided wall distillation column; and
recycling the recovered oxygenate reaction modifier or oxygenated byproducts to the fixed bed reactor, the second fixed bed reactor, the catalytic distillation reactor, or a combination thereof.

* * * * *